(12) United States Patent
Vander Meer et al.

(10) Patent No.: US 9,000,145 B2
(45) Date of Patent: Apr. 7, 2015

(54) CONTROL OF INSECT PESTS THROUGH RNAI OF PHEROMONE BIOSYNTHESIS ACTIVATING NEUROPEPTIDE RECEPTOR

(71) Applicant: The United States of America as represented by the Secretary of Agriculture, Washington, DC (US)

(72) Inventors: Robert K. Vander Meer, Newberry, FL (US); Man Yeon Choi, Gainesville, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/630,211

(22) Filed: Sep. 28, 2012

(65) Prior Publication Data

US 2014/0093474 A1 Apr. 3, 2014

(51) Int. Cl.
*C07H 21/02* (2006.01)
*C07H 21/04* (2006.01)
*C12P 19/34* (2006.01)
*A01N 25/00* (2006.01)
*A01N 57/16* (2006.01)

(52) U.S. Cl.
CPC .............. *C07H 21/02* (2013.01); *A01N 25/006* (2013.01); *A01N 57/16* (2013.01)

(58) Field of Classification Search
USPC ................... 435/6.1, 91.1, 91.31, 375, 468, 6; 536/24.3, 24.5, 23.1; 800/301, 302; 514/44
See application file for complete search history.

(56) References Cited

PUBLICATIONS

Choi et al, Proc. Nat'l. Acad. Sci., vol. 100, No. 17, pp. 9721-9726 (2003).*

* cited by examiner

*Primary Examiner* — Jane Zara
(74) *Attorney, Agent, or Firm* — John Fado; Albert Y. Tsui; Lesley Shaw (57) ABSTRACT

Disclosed are dsRNA constructs and methods to control insects via double stranded RNA interference of insect PBAN receptor genes.

3 Claims, 5 Drawing Sheets

CONTROL OF INSECT PESTS THROUGH RNAI OF PHEROMONE BIOSYNTHESIS ACTIVATING NEUROPEPTIDE RECEPTOR

FIELD OF THE INVENTION

This invention relates to dsRNA constructs and methods to control insects via double stranded RNA interference of insect PBAN receptor genes.

BACKGROUND OF INVENTION

Insect pests cost the general public billions of dollars annually in losses. These losses include the expense of controlling insect pests as well as crop loss and property damage caused by the pests. Economically significant insect pests in United States include *Solenopsis* spp. (fire ants) and moth species, such as *Helicoverpa zea* (commonly referred to as the cotton bollworm, corn earworm, or tomato fruitworm, depending on the plant the larvae are feeding on). For *Solenopsis invicta* specifically, the well-documented fire ant currently infests over 320 million acres in the United States and over $6 billion per year is spent for control, agricultural losses, medical costs, and damage repair (as reported in Lard, C. F., J. Schmidt, B. Morris, L. Estes, C. Ryan, and D. Bergquist. 2006. "An economic impact of imported fire ants in the United States of America." Texas A&M University, College Station, Tex. Available online at http://fireantecon.tamu.edu). Control of *Solenopsis invicta* is generally achieved through traditional chemical pesticides and/or delayed acting pesticides delivered as baits.

The insect pest *Helicoverpa zea* also has the capacity to inflict devastating yield losses to over 100 crop plants, the most important of which are corn, cotton, tomato, bean, broccoli, cabbage, eggplant, lettuce, okra, pea, pepper, soybean and watermelon. Due to its high multiplication rate, *H. zea* can rapidly build up large populations, so the feeding caterpillars can cause devastating crop losses. *Helicoverpa zea* is typically controlled through the use of pyrethroid and *Bacillus thuringiensis* (Bt) insecticides.

Chemical pesticides are the primary tools used to combat these insect pests. However, use of traditional chemical pesticides has disadvantages, including non-target effects on neutral or beneficial insects, as well as other animals. Chemical pesticide usage also can lead to chemical residue run-off into streams and seepage into water supplies resulting in ecosystem/environment damage. In addition, animals higher in the food chain are at risk when they consume pesticide contaminated crops or insects. The handling and application of chemical pesticides also presents exposure danger to the public and professionals, and could lead to accidental dispersal into unintended environmentally sensitive areas. In addition, prolonged chemical pesticide application may result in an insect population becoming resistance to a chemical pesticide. In order to control a traditionally chemical resistant-pest, new more potent chemical pesticides must be utilized, which in turn will lead to another resistance cycle. As such, there is a need in the art to control pest populations without the disadvantages of traditional chemical pesticides.

An approach to decrease dependence on chemical pesticides is by causing a specific gene(s) of the target-pest to malfunction by either over expression or silencing gene expression. The silencing approach utilizes RNA interference pathways to knockdown the gene of interest via double strand RNA. Double strand RNA (dsRNA) induces sequence-specific post-transcriptional gene silencing in many organisms by a process known as RNA interference (RNAi). RNAi is a post-transcriptional, highly conserved process in eukaryotes that leads to specific gene silencing through degradation of the target mRNA. The silencing mechanism is mediated by dsRNA that is homologous in sequence to the gene of interest. The dsRNA is processed into small interfering RNA (siRNA) by an endogenous enzyme called DICER inside the target pest, and the siRNAs are then incorporated into a multi-component RNA-induced silencing complex (RISC), which finds and cleaves the target mRNA. The dsRNA inhibits expression of at least one gene within the target, which exerts a deleterious effect upon the target.

Fire, et al. (U.S. Pat. No. 6,506,559) discloses a process of introducing RNA into a living cell to inhibit gene expression of a target gene in that cell. The RNA has a region with double-stranded structure. Inhibition is sequence-specific in that the nucleotide sequences of the duplex region of the RNA and of a portion of the target gene are identical. Specifically, Fire, et al. (U.S. Pat. No. 6,506,559) discloses a method to inhibit expression of a target gene in a cell, the method comprising introduction of a double stranded ribonucleic acid into the cell in an amount sufficient to inhibit expression of the target gene, wherein the RNA is a double-stranded molecule with a first ribonucleic acid strand consisting essentially of a ribonucleotide sequence which corresponds to a nucleotide sequence of the target gene and a second ribonucleic acid strand consisting essentially of a ribonucleotide sequence which is complementary to the nucleotide sequence of the target gene. Furthermore, the first and the second ribonucleotide strands are separately complementary strands that hybridize to each other to form the said double-stranded construct, and the double-stranded construct inhibits expression of the target gene.

To utilize RNA interference as a method to regulate gene expression for control, a specific essential gene needs to be targeted. Genes associated with signal transduction of neurohormones represent novel potential targets. One neurohormone gene family is the pheromone-biosynthesis-activating neuropeptide receptor (PBAN-R) gene family. Each PBAN-R is expressed in target tissue(s) in developmental and adult stages. The PBAN-R activates a specific physiological function after binding to a PBAN/pyrokinin peptide ligand. To date, over 200 PBAN/pyrokinin family peptide ligands have been identified. These peptide ligands/receptors have been shown to have a variety of functions in insects, such as: 1) stimulate pheromone biosynthesis in female moths (Raina et al., 1989); 2) induce melanization in moth larvae (Matsumoto et al., 1990; Altstein et al., 1996); 3) induce embryonic diapause and seasonal polyphenism in moths (Suwan et al., 1994; Uehara et al., 2011); 4) stimulate visceral muscle contraction (Nachman et al., 1986; Predel and Nachman, 2001); 5) accelerate puparium formation in several flies (Zdarek et al., 1997; Verleyen et al., 2004); 6) terminate pupal diapause in heliothine moths (Sun et al., 2003; Xu and Denlinger, 2003).

There is a need in the art to determine whether dsRNA interference of PBAN receptor expression interferes with essential developmental and/or reproductive functions of targeted insect pests and results in abnormal development and/or lack of reproduction. It has been reported in U.S. patent Ser. No. 13/323,880 (Vander Meer et al.) and Ser. No. 13/324,005 (Vander Meer et al.) that double-stranded ribonucleic acid construct that is complementary to a gene that encodes a PBAN/Pyrokinin gene sequence has a controlling effect on insects, e.g. *Solenopsis invicta* and *Helicoverpa zea*. However, there is a further need to determine whether dsRNA silencing of a PBAN receptor gene has an effect on controlling insects.

Furthermore there is a need for novel control methods that would interfere with essential developmental and/or reproductive functions of species that do not have the undesirable characteristics of traditional chemical pesticides. To that end, there is a need to develop dsRNA constructs that are engineered to interfere with essential developmental and/or reproductive functions of specific pest insects that would overcome some of the disadvantages of using traditional pesticides, specifically dsRNA interference of PBAN receptor gene expression.

BRIEF SUMMARY OF THE INVENTION

Disclosed herein is double-stranded ribonucleic acid (dsRNA) construct for inhibiting the expression of a pheromone-biosynthesis-activating neuropeptide receptor in a cell, wherein said dsRNA comprises a sense strand comprising a first sequence and an antisense strand comprising a second sequence complementary to SEQ. ID. NO. 2, wherein said first sequence is complementary to said second sequence. In one embodiment of the invention, the double-stranded ribonucleic acid is expressed in a plant cell.

Also disclosed herein is a double-stranded ribonucleic acid (dsRNA) construct for inhibiting the expression of a pheromone-biosynthesis-activating neuropeptide receptor in a cell, wherein said dsRNA comprises a sense strand comprising a first sequence and an antisense strand comprising a second sequence complementary to SEQ. ID. NO. 4, wherein said first sequence is complementary to said second sequence. In one embodiment of the invention, the double-stranded ribonucleic acid is expressed in a plant cell.

Disclosed herein is a method for controlling an insect, the method comprising: constructing a double stranded ribonucleic acid construct that is complementary to a gene that encodes an PBAN receptor gene sequence, dissolving the double stranded ribonucleic acid to form a solution, and contacting an effective amount of said solution to insect, wherein RNA interference is induced and insect control occurs. In one embodiment of the invention, the insect controlled is a *Solenopsis* spp. and the double stranded ribonucleic acid is complementary to the nucleotide sequence of SEQ. ID. NO. 2. In another embodiment of the invention, the insect controlled is a *Helicoverpa* spp. and the double stranded ribonucleic acid is complementary to the nucleotide sequence of SEQ. ID. NO. 4.

Also disclosed herein is a method for controlling an insect by dissolving double stranded ribonucleic acid to form a solution, contacting an effective amount of said solution to wherein the solution is applied to either to *Solenopsis* spp. bait material or *Helicoverpa* spp. bait material. In another embodiment of the invention, the bait material contains a phagostimulant. In yet another embodiment of the invention, the double stranded ribonucleic acid construct is dissolved in water.

Disclosed herein is a method for controlling a *Solenopsis* spp. with a double stranded ribonucleic acid construct, wherein pheromone production in *Solenopsis* spp. is decreased. In one embodiment of the invention, production of the recruitment pheromone Z,E-α-farnesene is decreased.

Also disclosed is a method for controlling a *Helicoverpa* spp. with a double stranded ribonucleic acid construct, wherein pheromone production in *Helicoverpa* spp. is decreased. In one embodiment of the invention, production of the cis-11-hexadecenal is decreased.

BRIEF DESCRIPTION OF THE DRAWINGS

The present invention together with the disclosed embodiments may best be understood from the following detailed description of the drawings, wherein.

BRIEF DESCRIPTION OF THE SEQUENCES

```
SEQ. ID. NO. 1:
ATGTTTTCGAGTAATACGATAACGAACATCACCTGGACCCTTCAGAATAG
GGATCCCTGGAGACTCCTGAAAGACGGCAATCTACAGGAATCTCGTTCCA
CGGTCGACGGTGTCGTTCACGCAAATCCAATATGAGAATTATACGAACAT
GCTCAGCCCCTTGCTTAGAGAAGAGAGCGCCGTTGATCGCCGGGACTCCC
TATACATCGTGCTGCCGATCACGGTGATTTACGTCGTGATCTTCTTCACC
GGCTATCGGCAATATCTCCACGTGCGTGGTAATCGCGCGCAACAAGTCCA
TGCACACCGCCACCAATTACTACCTCTTCAGCCTGGCGGTGTCCGACCTT
CTTCTACTCGTGTTCGGCCTGCCGCCGGAATTATTACATATGGTCGCACT
TTCCGTACATATTCGGCGAGGCGTTCTGCATTATACAGAGCTTCGCCTCG
GAGACCTCGGCGAACGCCACCGTTCTCACCATCACGGCCTTCACCATCGA
GAGATCGTGCGATTTGCCATCCCTTCATCTCGCACACAATGTCGAAACTC
TCCCGGGCGGTGAAGTTCGTGATAGCGATTTGGCTGCTGGCCCTCTGCTT
CGCCGTGCCACAGGCCATCCAATTCGGCATCTCTATCCCACTACAACGGC
ACTGTCATCTTGGATAGCGCCAGGTGCTCGCTGCGATGGACACTAATCGA
ACACGCCTTCGAGATCTCGACCTTCCTGTTCTTCGTGCTACCCATGACGA
TCATCACGTGCTTACGTGCTGATCGCCATCAAGCTGCGACACTCGAGCCT
GCTGACCACCGTCAGCAGTAAGAGGCATCACACTCCCGACGTGTTGAATC
ACGTAGACAGCAACAGGGGGAAAACGAATGCTCGAGAAAGTTATTCGCAT
GCTCGTTGCAGTAGTGGTAGCCTTTTTCATTTGTTGGGCGCCGTTTCACG
CTCAGAGATTGCTGGCTGTATACGCTCAGAGCAGTTCCGAGCCGCAAGAT
ACCATGGTCTAGTCTAACCACACTCACGTACGTGTCGGGAGTATTCTACT
ATTTATCCACCACGGTGAATCCGCTTCTCTACAATATCATGTCTAACAAG
TTCAGAGAAGCTTTCAAGTCGATGTTGCCTAAATATGTATCAGAAGTTCT
CATCTCACAAGGGCAACCGTCGACAACCGACTTACAGTAGCCTGTCGCGG
TATCACAGATCGATGAGACATCGATTTGATGACGCCCAGCACTCACCCTC
GATATCCGTTACGATGAACACAACGATTATCGCATATCGCATTGGCAAAC
GCAAATTCCTGTGAGCTGAATGGATTGGCGAAATTTCAGAACGAGAGAGA
GGGGCGACCTACGACCAGAGAAACCGTAGATTGTCGAATACCAGAAGATA
TCTAGAGATTCTGACTGCAGCCAACTTACCACGATGACATCGTTAAGCAA
ACAAGGTTTAAACAACGAAGGCAACAACAACGCAAATGAATGTCTACTGA
GAATTCACAGGTCCCGAAGGCTGTACTTTAGGAATCTTCACGGAGAGACT
GGGCCTCGGTACGAAAGGATTCTTCACACAACATCGGAAGATTTCATCGA
ACAATATGACGAAAATGACGAAGCCAAAACCGGAAAACGAATTGCGATGC
CCCACCTCTTGAGAGTCATCCGAGCATCGAGAGCGCCAATACGATTAGCA
ACTCTAGCCTTCAGGACCTCGACGAGACCGAATTCACGGGATCGGAATTG
GCGCGTTACATGGGCAGTTAAACTTCGACTTGTCACCTGA is the
PBAN receptor gene c -continued CGAAAAUGACGAAGCCAAAACCGGAAAACGUAAUUGCGAUGCCACCACCU
CUUGAGAGUC is a 5' to 3' construct forming one
strand of the dsRNA product referred to
as SoiPBAN-R dsRNA construct.

SEQ. ID. NO. 3:
ATGACATTGTCAGCGCCCCCGAGCATCGACGACTATGAAGATCCGTTCGT
GATGAACACGACGAACGTGACGAGCCACCCCGCCGCCTACGACGAGCAGT
ACGCGCTCGACCTGGTCGTGCCGCTCAGTCACCTATGTCATCATCTTCGT
GGCCGGCATCCTGGGAAACACCAGCACGTGTGTGGTCATAGCCAGGAACC
GCTCCATGCACACCGCCACCAACTTTTACCTGTTCAGTCTAGCAATATCA
GATTATATTATTAGTATGTGGCTTACCATTTGAAGTGCACAGATTATGGA
ATCCGGACACGTATCCGTTAGGCGAGGCGCACTGCATCGCCATCGGGCTG
GCGTCAGAGACGTCAGCCAACGCGACAGTTTACAATAACAGCGTTCACGG
TGGAGCGGTACATAGCGATATGTCGGCCCTTCATGTCGCACACCATGTCC
AAGCTGTCAAGAGCGGTGCGCTTCATCATAGCTATATGGGTGTTTGCATT
GTGTACGCGTGCCCCAGGCGATGCAGTTCGGTATAGTGTCGTATGTGGAT
CATGGGCAGAACGTGAGCGCGTGTACAGTGAAGGGTGTGGGGGTCCATCA
AGTGTTTGTTATATCTAGTTTCGTGTTCTTCTAGTCCTATGTCGATGATA
TCAGTGTTGTACGCGTTGATAGGCATTAAGTTACGGACCTCTCGAGTGTT
GCATCCCGTTAAGAAGCTGTCAGTGGAGAGCAATGAGAGACCTGGTCAGA
TGCAGTAAGAAAGGTGCGTCACAAAGAAGAGTCATCAGAATGCTCGTTGC
AGTGGCGCTATCATTCTTCATTTGCTGGGCGCCGTTCCACGTTCAAAGAC
TGCTGGCTATCTACGGGAAAAGCTTGGAGCACCATCAGAACCTTCTACTT
GGTCTACATCGTACTGACGTTTTTATCGGGGGTGCTATATTTCCTGTCGA
CCGCCATCAACCCCTTCCTATACAACATTATGTCGAACAAGTTCAGAAAC
GCCTTTAAGTTAAAACACAGCTTGA is the PBAN receptor
gene cDNA of Helicoverpa zea.

SEQ. ID. NO. 4:
GUGUUUGCAUUGUGUACCGCCGUGCCCCAGGCGAUGCAGUUCGGUAUAGU
GUCGUAUGUGGAUCAUGGGCAGAACGUGAGCGCGUGUACAGUGAAGGGUG
UGGGGGUCCAUCAAGUGUUUGUUAUAUCUAGUUUCGUGUUCUUCGUAGUG
CCUAUGGCGAUGAUAUCAGUGUUGUACGCGUUGAUAGGCAUUAAGUUACG
GACCUCUCGAGUGUUGCAUCCCGUUAAGAAGCUGUCAGUGGAGAGCAAUG
AGAGACCUGGUCAGAUGCAGUACAGAAAUGGUGCGUCACAAAGAAGAGUC
AUCAGAAUGCUCGUUGCAGUGGCGCUAUCAUUCUUCAUUUGCUGGGCGCC
GUUCCACGUUCAAAGACUGCUGGCUAUCUACGGGAAAAGCUUGGAGCACC
AUCAGAUACCUUCUACUUGGUCUACAUCGUACUGACGUUUUUAUCGGGG
GUGCUAUAUUUCCUGUCGACCGCCAUCAACCCCUUCCUAUA
is a 5' to 3' construct
forming one strand of the dsRNA
product referred to as HezPBAN-R dsRNA construct.

SEQ. ID. NO. 5:
AGGCTCTAGATTGTCTTAATTCGAGAGG CGACGTTCT
is a sense primer to construct dsRNA SoiPBAN-R.

SEQ. ID. NO. 6:
ATCCGCGGGTCTTAATTCGAGAGGCGACGTTCT
is an anti-sense primer to construct dsRNA
SoiPBAN-R.

SEQ. ID. NO. 7:
TTAAGTAAAATGGCATTGTCAGCG
is a sense primer to construct dsRNA HezPBAN-R.

SEQ. ID. NO. 8:
CAGACGAACGAACAAAAGGACTGCGA
is an anti-sense primer to construct dsRNA
HezPBAN-R.

SEQ. ID. NO. 9:
TAATACGACTCACTATAGGGACCGTCGACAACCGACTTAC
is a sense primer used to
construct DNA template of SoiPBAN-R dsRNA.

SEQ. ID. NO. 10:
TAATACGACTCACTATAGGGGACTCTCAAGAGGTGGTGGC
is an anti-sense primer used
to construct DNA template of SoiPBAN-R dsRNA.

SEQ. ID. NO. 11:
TAATACGACTCACTATAGGGGTGTTTGCATTGTGTACCGC
is a sense primer used to
construct DNA template of HezPBAN-R dsRNA.

SEQ. ID. NO. 12:
TAATACGACTCACTATAGGGTATAGGAAGGGGTTGATGGC
is an anti-sense primer -continued used to construct DNA template of
HezPBAN-R dsRNA.

SEQ. ID. NO. 13:
ATGCAYCANGCNCANAAYTAYTAYYTNTT
is a degenerate primer set.

SEQ. ID. NO. 14:
MHTATNYYLF is a peptide amplified by
SEQ. ID. NO. 13.

SEQ. ID. NO. 15:
GCRTGRAANGGNGCCCARCADATRAARAA is a degenerate
primer set.

SEQ. ID. NO. 16:
FFICWAPFHA is a peptide amplified by
SEQ. ID. NO. 15.

SEQ. ID. NO. 17:
TGTGATGCCTCTTACTGCTGACGGTGGTCA
is a primer used to amplify 5' cDNA ends.

SEQ. ID. NO. 18:
TAGTAATTGGTGGCGGTGCATGGACTT
is a primer used to amplify 5' cDNA ends.

SEQ. ID. NO. 19:
TTYTTYATHTGYTGGGCNCCNTTYCA
is a primer used to amplify 3' cDNA ends.

SEQ. ID. NO. 20:
CACCACGGTGAATCCGCTTCTCTACAATA
is a primer used to amplify 3' cDNA ends.

SEQ. ID. NO. 21:
TCAAGTCGATGTTGCCTAAATATTGTATC
is a primer used to amplify 3' cDNA ends.

SEQ. ID. NO. 22:
TAATACGACTCACTATAGGGACGTAAACGGCCACAAGTTC
is a primer used to amplify a GFP.

SEQ. ID. NO. 23:
TAATACGACTCACTATAGGGTGCTCAGGTAGTGGTTGTCG
is a primer used to amplify a GFP.

DETAILED DESCRIPTION OF THE INVENTION

Disclosed here are specific insect pest dsRNA constructs that target PBAN receptor gene expression. Using dsRNA inhibiting expression of the PBAN receptor gene as a means of interfering with critical functions of the PBAN receptor/ligand system, a novel method to develop nucleic acid control for pest management is disclosed.

Definitions

As used in the specification and claims, the singular form "a", "an" and "the" include plural references unless the context clearly dictates otherwise. For example, the term "a cell" includes a plurality of cells, including mixtures thereof.

The term "gene" refers to a DNA sequence involved in producing a polypeptide or precursor thereof. The polypeptide can be encoded by a full-length coding sequence or by any portion of the coding sequence, such as exon sequences. In one embodiment of the invention, the gene target is a PBAN receptor gene of an insect.

The term "pheromone-biosynthesis-activating neuropeptide receptor" refers to a G-Protein coupled receptor, also known as a seven-transmembrane domain receptor, whose activating ligand(s) is derived from the 4 to 5 peptides produced by the PBAN/pyrokinin gene.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. The present invention embodies utilizing the oligonucleotide in the form of dsRNA as means of interfering with a critical developmental or reproductive process that leads to control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "double stranded RNA" or "dsRNA" refers to two substantially complementary strands of ribonucleic acid. "Identity," as used herein, is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M Stockton Press, New York (1991)). Methods commonly employed to determine identity between sequences include, for example, those disclosed in Carillo, H., and Lipman, D., *SIAM J. Applied Math.* (1988) 48:1073. "Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene, provided that the mismatches occur at a distance of at least three nucleotides from the fusion site.

As used herein, "target gene" refers to a section of a DNA strand of a double-stranded DNA that is complementary to a section of a DNA strand, including all transcribed regions, that serves as a matrix for transcription. The target gene is therefore usually the sense strand.

The term "complementary RNA strand" refers to the strand of the dsRNA, which is complementary to an mRNA transcript that is formed during expression of the target gene, or its processing products. "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA.

As used herein, the term "GFP dsRNA" refers to a control dsRNA construct. The green fluorescent protein (GFP) is commonly used as a reporter gene and was originally isolated from jellyfish and widely used as control in prokaryotic and eukaryotic systems.

"Small interfering RNA" or "siRNA" refers to a short double-strand of ribonucleic acid, approximately 18 to 30 nucleotides in length. The term "RNA interference" or "RNAi" refers to a cellular mechanism for the destruction of targeted ribonucleic acid molecules. Under endogenous conditions, RNAi mechanism operates when dsRNA is cleaved to siRNA via an enzyme, DICER. The siRNA is processed to a single strand of anti-sense ribonucleic acid and coupled with a protein complex named RISC. The antisense RNA then targets a complementary gene construct, such as messenger RNA that is cleaved by ribonuclease. While the examples infra discloses constructing dsRNA constructs via enzymatic techniques with the enzyme RNA polymerase, it is contemplated that siRNA can be constructed via RNA oligonucleotide synthesis such as those disclosed in Scaringe, S., Methods Enzymol., 2000, Vol. 317:3 and incorporated herein by reference.

As used herein, "knock-down" is defined as the act of binding an oligonucleotide with a complementary nucleotide sequence of a gene as such that the expression of the gene or mRNA transcript decreases. In an embodiment, knock-down of a PBAN receptor gene occurs via injection of a dsRNA that can have multiple negative effects on the target insect, such the insect control occurs.

The term "insect-control" with dsRNA, as used herein, refers to the capacity to inhibit normal insect pupae and larvae development, make the insect infertile, inhibit pheromone production, induce mortality in the insect, affect growth in such a manner that the pest insect population becomes economically unimportant. Results for controlling said insect include, but not limited to, causing mortality to the insect, having the insect produce fewer offspring, are less fit or making the insect more susceptible to predator/parasite or pathogen attack. Insect control of *Helicoverpa zea* at the larval stage decreased feeding thus inhibit growth of the insect. For *Helicoverpa zea*, inhibition of pheromone production interferes with the insect mating process in general. For *Solenopsis invicta*, inhibition of recruitment pheromone production makes workers less fit to bring resources back to the colony or to initiate critical colony migration.

The term "substantially single-stranded" when used in reference to a nucleic acid product means that the product molecule exists primarily as a single strand of nucleic acid in contrast to a double-stranded product which exists as two strands of nucleic acids which are held together by interstrand base pairing interactions.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA".

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target insect wherein critical developmental and/or reproductive functions of said insect are disrupted as a result of ingestion.

The term "solvent" includes any liquid that holds another substance in solution. Examples of solvents include but are not limited to water and organic solvents such as acetone, ethanol, dimethyl sulfoxide (DMSO), and dimethylformamide (DMF).

The term "phagostimulant" refers to any substance that will entice the insect to ingest the dsRNA. For insects, suitable phagostimulants include but are not limited to syrups, honey, aqueous solutions of sucrose, artificial sweeteners such as sucralose, saccharin, and other artificial sweeteners, amino acids, and other proteins. Additionally, the bait material containing the dsRNA constructs disclosed herein would be incorporated in water soluble baits, oil-in water or oil/water emulsion baits, liquid type or gel type of baits.

Methods which are well known to those skilled in the art may be used to construct expression vectors containing sequences encoding PBAN receptor gene and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) Current Protocols in Molecular Biology, John Wiley & Sons, New York, N.Y.

dsRNA containing a nucleotide sequence complementary to a portion of the PBAN receptor target gene is preferred to induce insect mortality. As disclosed herein, 100% sequence identity between the RNA and the target gene is not required to practice the present invention. Thus, the invention has the advantage of being able to tolerate sequence variations that might be expected due to genetic mutation, strain polymorphism, or evolutionary divergence. RNA sequences with insertions, deletions, and single point mutations relative to the target sequence may also be effective for insect mortality.

Thus, sequence identity may be optimized by sequence comparison and alignment algorithms known in the art. Thus, the determination of percent identity between any two sequences can be accomplished using a mathematical algorithm. Non-limiting examples of such mathematical algorithms are the algorithm of Myers and Miller (1988. CABIOS 4: 11-17), the local homology algorithm of Smith et al. (1981. Adv. Appl. Math. 2: 482); the homology alignment algorithm of Needleman and Wunsch (1970. J. Mol. Biol. 48: 443-453); the search-for-similarity-method of Pearson and Lipman (1988. Proc. Natl. Acad. Sci. 85: 2444-2448; the algorithm of Karlin and Altschul (1990. Proc. Natl. Acad. Sci. USA 87: 2264), modified as in Karlin and Altschul (1993. Proc. Natl. Acad. Sci. USA 90: 5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Greater than 90% sequence identity, or even 100% sequence identity, between the inhibitory RNA and the portion of the PBAN receptor target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60° C. hybridization for 12-16 hours; followed by washing). The length of the substantially identical double-stranded nucleotide sequences may be at least about 18, 19, 21, 25, 50, 100, 200, 300, 400, 491, 500, or 510 bases. In a preferred embodiment, the length of the double-stranded nucleotide sequence is approximately from about 18 to about 510 nucleotides in length for *Solenopsis invicta*. In a preferred embodiment, the length of the double-stranded nucleotide sequence is approximately from about 18 to about 491 nucleotides in length for *Helicoverpa zea*.

The dsRNA construct disclosed herein may optionally comprise a single stranded overhang at either or both ends. The double-stranded structure may be formed by a single self-complementary RNA strand (i.e. forming a hairpin loop) or two complementary RNA strands. RNA duplex formation may be initiated either inside or outside the cell. When the dsRNA of the invention forms a hairpin loop, it may optionally comprise an intron, as set forth in U.S. 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559. The RNA may be introduced in an amount that allows delivery of at least one copy per cell. Expression of higher doses of double-stranded construct may yield more effective insect mortality.

While the examples provided wherein describe dsRNA constructs targeting PBAN receptor genes (GenBank Accession Nos. AY319852 and JX657040), it is contemplated that when read in conjunction with the teaching disclosed herein, the construction of other dsRNA constructs targeting PBAN receptor gene sequences of other insects would be feasible to those skilled in the art. As used herein, "SoiPBAN-R dsRNA" refers to dsRNA construct synthesized from SEQ. ID. NO. 2.

As used herein, "HezPBAN-R dsRNA" refers to dsRNA construct synthesized from SEQ. ID. NO. 4.

Additionally it is contemplated that the disclosure herein would teach the transfer of a nucleic acid fragment into the genome of a host organism, resulting in genetically stable inheritance, particularly in a plant. Host organisms containing the transformed nucleic acid fragments are referred to as "transgenic" organisms. Examples of methods of plant transformation include Agrobacterium-mediated transformation (De Blaere et al. 1987. Meth. Enzymol. 143: 277) and biolistic particle delivery or "gene gun" transformation technology (Klein et al. 1987. Nature (London) 327: 70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transformation of plant cells or for the establishment of transgenic plants have been described in, e.g., Pouwels et al. 1985. Supp. 1987. Cloning Vectors: A Laboratory Manual; Weissbach and Weissbach. 1989. Methods for Plant Molecular Biology, Academic Press, New York; and Flevin et al. 1990. Plant Molecular Biology Manual, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

All *S. invicta* samples were collected from monogyne (single functional queen) colonies collected from the Gainesville, Fla. USA area by excavation of nests or by establishing colonies directly from newly mated queens and maintained as described in W. A Banks et al., "Techniques for collecting, rearing, and handling imported fire ants" (USDA, SEA, AATS-S-21, 9 p., 1981).

Pupae of the corn earworm, *H. zea*, were purchased from Bio-Sery (Frenchtown, N.J., USA) and maintained at room temperature under a L/D regimen of 15:9 until they emerged as adults. Female pupae or virgin adults were used for dsRNA injection or sex pheromone analysis.

SoiPBAN-R Cloning: Poly(A) RNA was isolated from whole body and head of *S. invicta* workers and female alates to synthesize cDNA as described previously in M. Y. Choi, et. al, Proc Natl Acad Sci, USA 100, 9721 (2003). Synthesized cDNA was amplified with a degenerate primer set: ATGCAY-CANGCNCANAAYTAYTAYYTNTT (SEQ. ID. NO. 13) (MHTATNYYLF) (SEQ. ID. NO. 14) and GCRTGRAANG-GNGCCCARCADATRAARAA (SEQ. ID. NO. 15) (FFICWAPFHA) (SEQ. ID. NO. 16) mostly conserved in TM2 and TM7 of PBAN GPCRs. PCR was performed for 35 cycles at 95° C. for 30 s, 50° C. for 30 s, and 72° C. for 1 min. The PCR product was directly sequenced and used to design further gene-specific primers to find 5'- and 3'-ends of the SoiPBAN-R cDNA. 5'-RACE (RACE kit Invitrogen) was performed using primers TGTGATGCCTCTTACTGCT-GACGGTGGTCA (SEQ. ID. NO. 17) (from nucleotide 1106) and TAGTAATTGGTGGCGGTGTGCATGGACTT (SEQ. ID. NO. 18) (from nucleotide 588) by 5'-RACE kit (Invitrogen). 3'-RACE was performed using primers TTYT-TYATHTGYTGGGCNCCNTTYCA (SEQ. ID. NO. 19) (from nucleotide 1199), 5'-CACCACGGTGAATCCGCT-TCTCTACAATA (SEQ. ID. NO. 20) (from nucleotide 1336) and TCAAGTCGATGTTGCCTAAATATTGTATC (SEQ. ID. NO. 21) (from nucleotide 1392). Then PCR products were cloned and confirmed by DNA sequence (ICBR, University of Florida). Sequences of the receptor DNA and amino acid were analyzed by a Genetyx software ver. 10 (Genetyx Corporation).

EXAMPLE 1

Constructing SoiPBAN-R dsRNA Construct

SoiPBAN-R dsRNA was synthesized from the full length Soi-PBAN cDNA (531-bp) using specific 5'-T7-appended (underlined) primers (<u>TAATACGACTCACTATAGGG</u>ACCGTCGACAACCGACTTAC (SEQ. ID. NO. 9) and 5'-<u>TAATACGACTCACTATAGGG</u>GACTCTCAAGAGGTGG TGGC (SEQ. ID. NO. 10)) to amplify a 510-bp SoiPBAN-R DNA fragment. This fragment served as the template for dsRNA synthesis using the MEGAscript RNA kit (Ambion, Austin, Tex., USA). Green fluorescence protein (GFP) dsRNA served as the negative dsRNA control and was either purchased (Ambion) or was synthesized from a 546-bp GFP DNA template amplified by these primers, <u>TAATACGACTCACTATAGGG</u>ACGTAAACGGCCACAA GTTC (SEQ. ID. NO. 22) and <u>TAATACGACTCACTATAGGG</u>TGCTCAGGTAGTGGTT GTCG (SEQ. ID NO. 23), using the same kit as above.

EXAMPLE 2

HezPBAN-R dsRNA Construct

The brain-subesophageal ganglia (Br-SGs) of 1 to 3-day old *H. zea* female moths were dissected to isolate mRNA for synthesis of cDNA using Invitrogen MicroFast mRNA purification kits and GeneRacer cDNA synthesis kits to clone the full length HezPBAN-R cDNA. The primer set: 5'-TTA AGT AAA ATG GCA TTG TCA GCG-3' and 5'-CAGAC GAA CGA ACA AAA GGA CTG CGA-3' was designed from the sequence deposited in GenBank (Accession number: AY319852). PCR was performed with the following temperature program: 33 cycles at 95° C. for 30 s, 55° C. for 30 s, and 72° C. for 1 min. The full length PCR product was gel purified and cloned using TOPO TA cloning kit (Invitrogen) and sequenced. To construct HezPBAN-R dsRNA, a PCR primer set was designed, T7-appended (underlined): TAATACGACTCACTATAGGGGTGTTTGCATTGTGTAC CGC (SEQ. ID. NO. 11) and TAATACGACTCACTATAGGGTATAGGAAGGGGT-TGATGGC (SEQ. ID. NO. 12), to amplify a 491-bp DNA fragment, which served as the template for dsRNA synthesis using the MEGAscript RNA kit (Ambion). The negative dsRNA control was dsGFP constructed by the same method described above in Example 1. The length of Hez-PBAN dsRNA was synthesized from the full length of Hez-PBAN cDNA, 585-bp

EXAMPLE 3

Injection SoiPBAN-R dsRNA to Adult *Solenopsis invicta* and Pupae Bioassay

Figure 1:
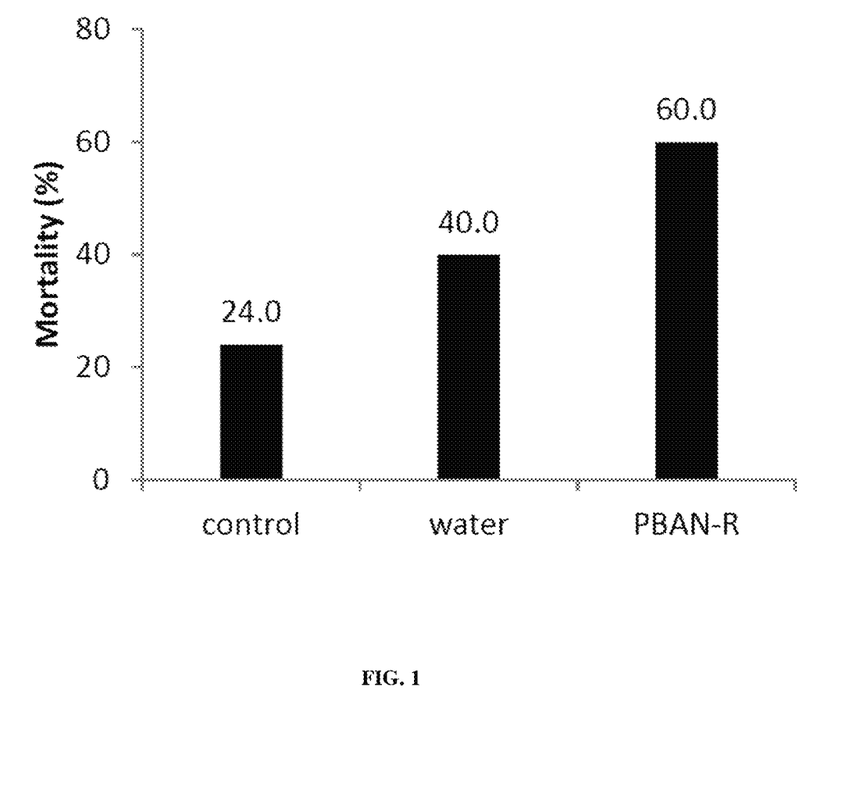
FIG. 1 is a graph depicting mortality percentage of injecting either water, GFP dsRNA (control), or SoiPBAN-R dsRNA in *Solenopsis invicta* female alate pupae.

SoiPBAN-R dsRNA was injected into the hemocoel of *S. invicta* adult workers and female alate pupae using a Nano-liter 2000™ System using pulled borosilicate needles (World Precision Instruments, Sarasota, Fla., USA). SoiPBAN-R dsRNA (20 ng/50 nL/ant), GFP dsRNA (20 ng/50 nL/ant), and water (50 nL/ant) were each injected into 10 young adult workers (brood tenders) and 25 female alate pupae (48-72 h after pupation). Results of the injection are depicted in FIG. 1. Workers were observed for mortality for eight-ten days post-injection. Injected pupae were observed for delay of cuticle melanization (cuticle tanning) and mortality until adult emergence, about eight days.

EXAMPLE 4

SoiPBAN-R dsRNA *Solenopsis invicta* Sucrose Feeding Bioassay

Figure 2:
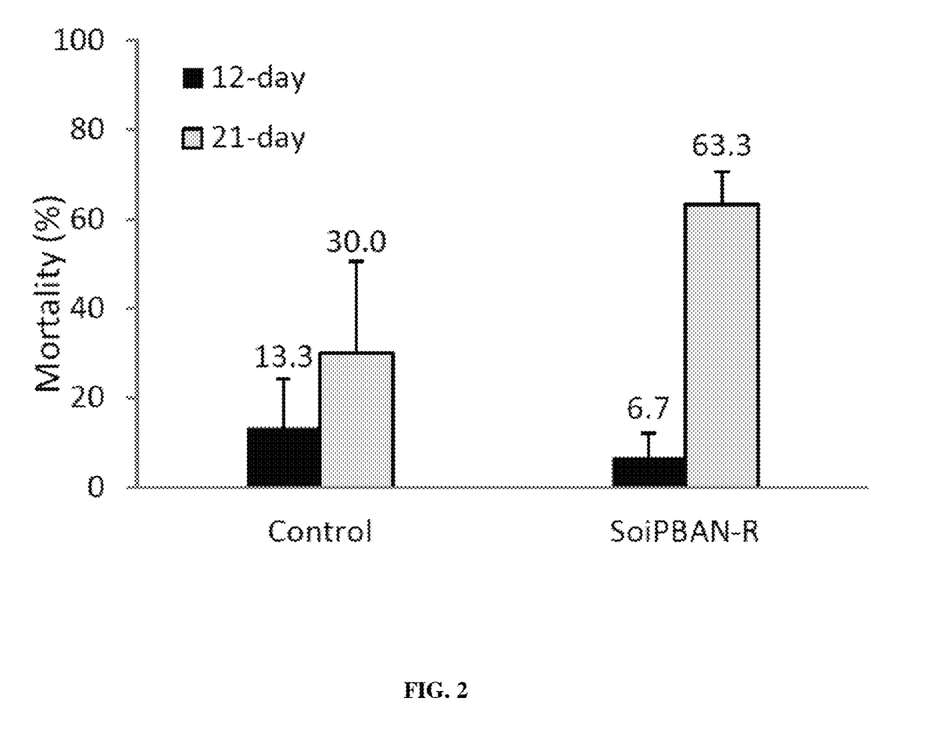
FIG. 2 is a graph depicting mortality percentage of feeding either water, GFP dsRNA (control), or SoiPBAN-R dsRNA to *Solenopsis invicta* worker larvae.

SoiPBAN-R dsRNA (1 μg/μL) was dissolved in 10% sucrose solution (wt./vol.) and provided for a period of 12 days via a capillary tube to six nurse worker that were caring for ten 4$^{th}$ instar larvae. Following the initial 12-day feeding period, the nurse workers were fed only 10% sucrose solution without dsRNA and observed for an additional 9 days. The fire ant larval mortality was recorded. Results of the feeding bioassay are depicted in FIG. 2.

EXAMPLE 5

Inhibition of Recruitment Pheromone Production Via SoiPBAN-R dsRNA in Bioassay

To evaluated the effect of SoiPBAN-R dsRNA on the recruitment pheromone production, Z,E-α-farnesene levels in adult *Solenopsis invicta* worker Dufour's gland after SoiP-BAN injection and saline injected controls.

All dissections were performed using a Zeiss Stemi SV 6 stereo microscope at 25× magnification. A drop of water was placed on the surface of a homemade silicon filled petridish (85 mm dia.). A decapitated ant was held at the anterior end of the gastor just below the petiole in the drop of water with #5 Dumont jewelers' forceps. Six separate drops of water were placed on the Petri dish, one for each ant dissected. With a second pair of forceps the last segment of cuticle on the dorsal side of the gastor was gently opened and removed, exposing the sting. The sting was grasped and gently pulled away, yielding the sting (S), the poison gland/sac (PG), and the Dufour's gland (DG). Forceps were cleaned in 10% bleach between dissections for poison sac, dufour's gland and sting apparatus, and between ants to avoid cross contamination. The DG is a small gland usually covered in fat bodies and is located at the base of the sting. The gland was pinched off at its base with the forceps and gland presence on the forceps was confirmed under the microscope. After six dissections were completed the Petri dish was cleaned with 10% bleach before the next group of dissections. The glands were immediately placed in a RNase free micro-centrifuge tube on dry ice and kept at −80° C. until use. For GC analysis, a DG was placed in a 100 μL vial insert containing 50 μL hexane and 50 ng C16 as internal standard. The insert was placed in a 2 ml vial containing a small amount of hexane, which acted to slow solvent evaporation. Samples were held at −20° C. until use.

Figure 3A:
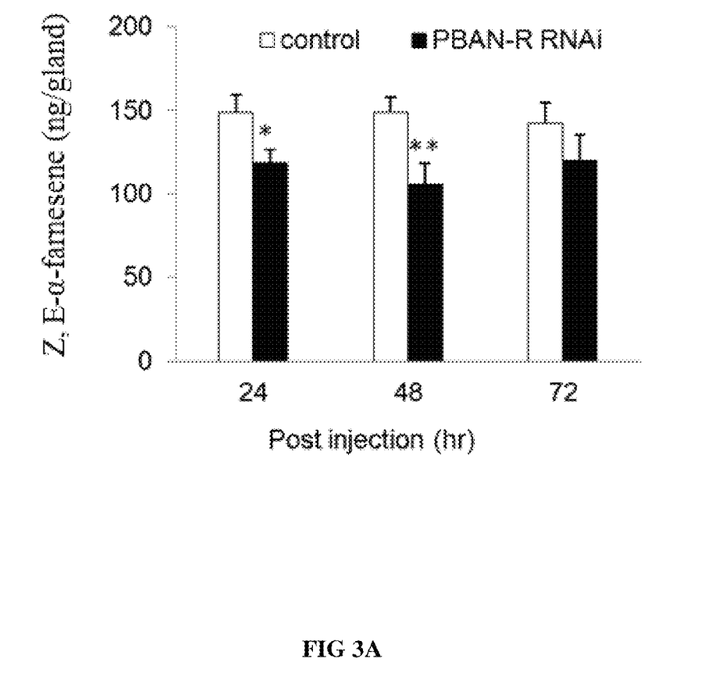
FIG. 3A is a graph quantifying the recruitment pheromone, Z,E-α-farnesene, in *Solenopsis invicta* adult workers after injection with 1 μg (50 nL) of SoiPBAN-R dsRNA and control over a period of 72 hours. Each treatment was replicated at least 10 times. Single asterisk, $P<0.005$; Double asterisks, $P<0.001$ from unpaired t-test (two-tailed) analysis.

Injection of SoiPBAN-R dsRNA (1 ug) into workers resulted in significant reduction of recruitment pheromone production starting at 24-hr (FIG. 3A; RNAi vs. control, 118±8.1 ng vs. 149±10.6 ng per worker, respectively, P=0.030, n=10), and reached a maximum at 48 hr post-injection (FIG. 3A; RNAi vs. control: 106±13.0 ng vs. 149±9.2 ng per worker, P=0.013, n=10). By the 72-hr evaluation period pheromone production was no longer significantly different from control (RNAi vs. control: 120±15.7 ng vs. 143±12.0 ng per worker, respectively, P=0.255, n=10). The RNAi experiments demonstrated that suppression of SoiPBAN-R gene transcription temporarily reduced pheromone production by decreasing the number of receptors available for PBAN neuropeptide ligands that would normally activate pheromone biosynthesis.

Figure 3B:
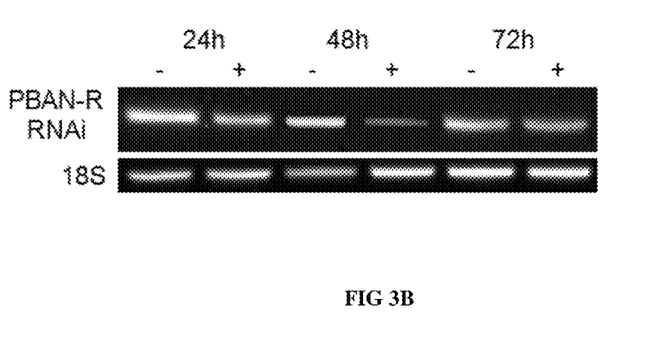
FIG. 3B is an electrophoresis photo showing that SoiPBAN-R expression is suppressed in the Dufour's gland (source of recruitment pheromone) after SoiPBAN-R dsRNA treatment.

To investigate the transcription level of SoiPBAN-R, worker fire ants (~100) were injected with SoiPBAN-R dsRNA (1 μg), then sacrificed to collect Dufour's glands at 24, 48, and 72 h after treatment. The receptor gene transcription levels from each time period were observed using RT-PCR. The reduction in gene expression was particularly apparent at 48-hr post injection (FIG. 3B), corresponding to the incubation time that resulted in the greatest pheromone reduction (FIG. 3A).

EXAMPLE 6

Inhibition of Pheromone Production Via HezPBAN-R dsRNA in Bioassay

Figure 4:
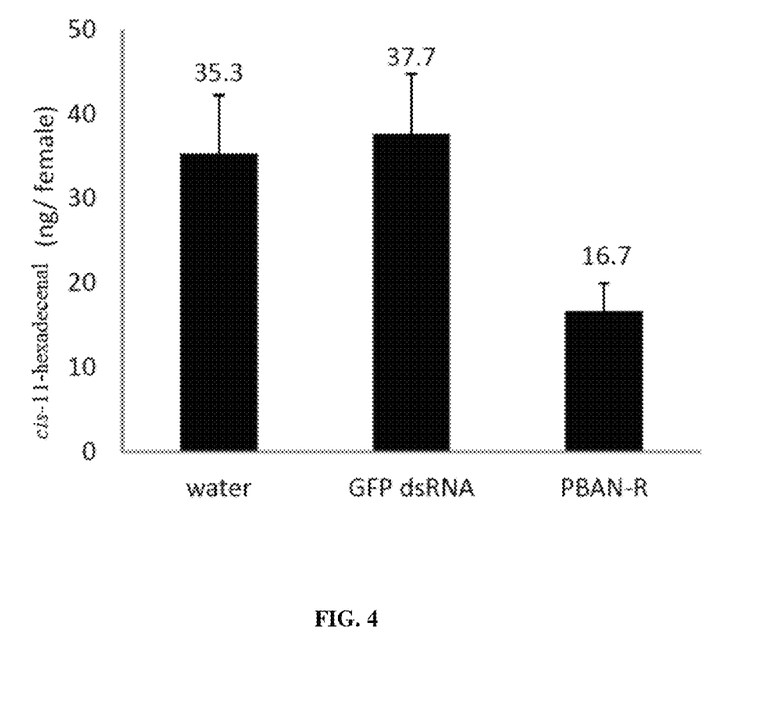
FIG. 4 is a graph depicting pheromone production of cis-11-hexadecenal in adult *Helicoverpa zea* after injection with either water, GFP dsRNA (control), or dsRNA HezPBAN-R.

Emerged female adults from the three groups were used to extract and quantify the amount of sex pheromone, cis-11-hexadecenal (Z11-16:Ald, major component) produced. The sex pheromone was extracted 2-4-hr after lights-off in the $2^{nd}$-$3^{rd}$ scotophase after adult emergence. The *H. zea* pheromone glands were dissected and soaked in a hexane containing 100 ng cis-9-tetradecenal (Z9-14:Ald) as an internal standard. The gland extracts were analyzed by an Agilent 6890N gas chromatography (GC) with a flame ionization detector and a DB-23 (J&W, Santa Clara, Calif., USA) capillary column (30 m×0.25 mm). Results showing pheromone production for treatment and controls are depicted in FIG. 4. The GC oven temperature was programmed at 80° C. for 1 min, then 10° C./min to 230° C. and held for 8 min. The cis-11-hexadecenal was identified based on comparison of retention time with that of synthetic cis-11-hexadecenal (Bedoukian, Danbury, Conn., USA).

While the invention has been described with reference to details of the illustrated embodiment, these details are not intended to limit the scope of the invention as defined in the appended claims. The embodiment of the invention in which exclusive property or privilege is claimed is defined as follows:

SEQUENCE LISTING

<160> NUMBER OF SEQ ID NOS: 23

<210> SEQ ID NO 1
<211> LENGTH: 1790
<212> TYPE: DNA
<213> ORGANISM: Artificial Sequence
<220> FEATURE:
<223> OTHER INFORMATION: PBAN receptor gene cDNA of Solenopsis invicta

<400> SEQUENCE: 1

| | | | | | |
|---|---|---|---|---|---|
| atgttttcga | gtaatacgat | aacgaacatc | acctggaccc | ttcagaatag | ggatccctgg | 60 |
| agactcctga | aagacggcaa | tctacaggaa | tctcgttcca | cggtcgacgg | tgtcgttcac | 120 |
| gcaaatccaa | tatgagaatt | atacgaacat | gctcagcccc | ttgcttagag | aagagagcgc | 180 |
| cgttgatcgc | cgggactccc | tatacatcgt | gctgccgatc | acggtgattt | acgtcgtgat | 240 |
| cttcttcacc | ggctatcggc | aatatctcca | cgtgcgtggt | aatcgcgcgc | aacaagtcca | 300 |
| tgcacaccgc | caccaattac | tacctcttca | gcctggcggt | gtccgacctt | cttctactcg | 360 |
| tgttcggcct | gccgccggaa | ttattacata | tggtcgcact | ttccgtacat | attcggcgag | 420 |
| gcgttctgca | ttatacagag | cttcgcctcg | gagacctcgg | cgaacgccac | cgttctcacc | 480 |
| atcacggcct | tcaccatcga | gagatcgtgc | gatttgccat | cccttcatct | cgcacacaat | 540 |
| gtcgaaactc | tcccgggcgg | tgaagttcgt | gatagcgatt | tggctgctgg | ccctctgctt | 600 |
| cgccgtgcca | caggccatcc | aattcggcat | ctctatccca | ctacaacggc | actgtcatct | 660 |
| tggatagcgc | caggtgctcg | ctgcgatgga | cactaatcga | acacgccttc | gagatctcga | 720 |
| ccttcctgtt | cttcgtgcta | cccatgacga | tcatcacgtg | cttacgtgct | gatcgccatc | 780 |
| aagctgcgac | actcgagcct | gctgaccacc | gtcagcagta | agaggcatca | cactcccgac | 840 |
| gtgttgaatc | acgtagacag | caacagggg | aaaacgaatg | ctcgagaaag | ttattcgcat | 900 |
| gctcgttgca | gtagtggtag | cctttttcat | ttgttgggcg | ccgtttcacg | ctcagagatt | 960 |
| gctggctgta | tacgctcaga | gcagttccga | gccgcaagat | accatggtct | agtctaacca | 1020 |
| cactcacgta | cgtgtcggga | gtattctact | atttatccac | cacggtgaat | ccgcttctct | 1080 |
| acaatatcat | gtctaacaag | ttcagagaag | ctttcaagtc | gatgttgcct | aaatatgtat | 1140 |
| cagaagttct | catctcacaa | gggcaaccgt | cgacaaccga | cttacagtag | cctgtcgcgg | 1200 |
| tatcacagat | cgatgagaca | tcgatttgat | gacgcccagc | actcaccctc | gatatccgtt | 1260 |
| acgatgaaca | caacgattat | cgcatatcgc | attggcaaac | gcaaattcct | gtgagctgaa | 1320 |
| tggattggcg | aaatttcaga | acgagagaga | ggggcgacct | acgaccagag | aaaccgtaga | 1380 |
| ttgtcgaata | ccagaagata | tctagagatt | ctgactgcag | ccaacttacc | acgatgacat | 1440 |
| cgttaagcaa | acaaggttta | aacaacgaag | gcaacaacaa | cgcaaatgaa | tgtctactga | 1500 |
| gaattcacag | gtcccgaagg | ctgtacttta | ggaatcttca | cggagagact | gggcctcggt | 1560 |
| acgaaaggat | tcttcacaca | acatcggaag | atttcatcga | acaatatgac | gaaaatgacg | 1620 |
| aagccaaaac | cggaaaacga | attgcgatgc | cccacctctt | gagagtcatc | cgagcatcga | 1680 |
| gagcgccaat | acgattagca | actctagcct | tcaggacctc | gacgagaccg | aattcacggg | 1740 |
| atcggaattg | gcgcgttaca | tgggcagtta | aacttcgact | tgtcacctga | | 1790 |

<210> SEQ ID NO 2
<211> LENGTH: 510
<212> TYPE: RNA
<213> ORGANISM: Artificial Sequence
<220> FEATURE:
<223> OTHER INFORMATION: construct forming one strand of the dsRNA product referred to as SoiPBAN-R dsRNA construct

<400> SEQUENCE: 2

| accgucgaca accgacuuac aguagccugu cgcgguauca cagaucgaug agacaucgau | 60 |
| uugaugacgc ccagcacuca cccucgauau ccguuagcga ugaacaucaa cgauuaucgc | 120 |
| auaucgcauu ggcaaacgca aauccugug agcugaaugg auuggcgaaa uuucagaacg | 180 |
| agagagaggg gcgaccuacg accagagaaa ccguagauug ucgagauacc agaagaauau | 240 |
| cuagagauuc ugacugcagc caacuuacca cgaugacauc guuaagcaaa caagguuuaa | 300 |
| acaacgaagg caacaacaac gcaaaugaau gucuacugag aauucacagg ucaccgaagg | 360 |
| cugucacuuu aggaaucuuc acggagagac ugggccucgg uacgaaagga uucuucacac | 420 |
| aacaucggaa gauuucaucg aacaauauga cgaaaaugac gaagccaaaa ccggaaaacg | 480 |
| uaauugcgau gccaccaccu cuugagaguc | 510 |

<210> SEQ ID NO 3
<211> LENGTH: 1025
<212> TYPE: DNA
<213> ORGANISM: Artificial Sequence
<220> FEATURE:
<223> OTHER INFORMATION: PBAN receptor gene cDNA of Helicoverpa zea

<400> SEQUENCE: 3

| atgacattgt cagcgccccc gagcatcgac gactatgaag atccgttcgt gatgaacacg | 60 |
| acgaacgtga cgagccaccc cgccgcctac gacgagcagt acgcgctcga cctggtcgtg | 120 |
| ccgctcagtc acctatgtca tcatcttcgt ggccggcatc ctgggaaaca ccagcacgtg | 180 |
| tgtggtcata gccaggaacc gctccatgca caccgccacc aactttttacc tgttcagtct | 240 |
| agcaatatca gattatatta ttagtatgtg gcttaccatt tgaagtgcac agattatgga | 300 |
| atccggacac gtatccgtta ggcgaggcgc actgcatcgc catcgggctg cgtcagaga | 360 |
| cgtcagccaa cgcgacagtt tacaataaca gcgttcacgg tggagcggta catagcgata | 420 |
| tgtcggccct tcatgtcgca caccatgtcc aagctgtcaa gagcggtgcg cttcatcata | 480 |
| gctatatggg tgtttgcatt gtgtacgcgt gccccaggcg atgcagttcg gtatagtgtc | 540 |
| gtatgtggat catgggcaga acgtgagcgc gtgtacagtg aagggtgtgg ggtccatca | 600 |
| agtgtttgtt atatctagtt tcgtgttctt ctagtcctat gtcgatgata tcagtgttgt | 660 |
| acgcgttgat aggcattaag ttacggacct ctcgagtgtt gcatcccgtt aagaagctgt | 720 |
| cagtggagag caatgagaga cctggtcaga tgcagtaaga aaggtgcgtc acaaagaaga | 780 |
| gtcatcagaa tgctcgttgc agtggcgcta tcattcttca tttgctgggc gccgttccac | 840 |
| gttcaaagac tgctggctat ctacgggaaa agcttggagc accatcagaa ccttctactt | 900 |
| ggtctacatc gtactgacgt ttttatcggg ggtgctatat ttcctgtcga ccgccatcaa | 960 |
| ccccttccta tacaacatta tgtcgaacaa gttcagaaac gcctttaagt taaaacacag | 1020 |
| cttga | 1025 |

<210> SEQ ID NO 4
<211> LENGTH: 491
<212> TYPE: RNA
<213> ORGANISM: Artificial Sequence
<220> FEATURE:
<223> OTHER INFORMATION: construct forming one strand of the dsRNA
       product referred to as HezPBAN-R dsRNA construct

<400> SEQUENCE: 4

```
guguuugcau uguguaccgc cgugcccag gcgaugcagu ucgguauagu gucguaugug    60
gaucaugggc agaacgugag cgcguguaca gugaagggug uggggguccau caaguguuu   120 guuauaucua guuucguguu cuucguagug ccuaugucga ugauaucagu guugacgcg   180 uugauaggca uuaaguuacg gaccucucga guguugcauc ccguuaagaa gcugucagu   240 gagagcaaug agagaccugg ucagaugcag uacagaaaug gugcgucaca aagaagaguc   300
aucagaaugc ucguugcagu ggcgcuauca uucuucauuu gcugggcgcc guuccacguu   360
caaagacugc uggcuaucua cgggaaaagc uuggagcacc caucagauac cuucuacuug   420
gucuacaucg uacgacguu uuuaucgggg gugcuauauu uccugucgac cgccaucaac   480
cccuuccuau a                                                       491

<210> SEQ ID NO 5
<211> LENGTH: 37
<212> TYPE: DNA
<213> ORGANISM: Artificial Sequence
<220> FEATURE:
<223> OTHER INFORMATION: sense primer to construct dsRNA SoiPBAN-R

<400> SEQUENCE: 5
aggctctaga ttgtcttaat tcgagaggcg acgttct                            37

<210> SEQ ID NO 6
<211> LENGTH: 33
<212> TYPE: DNA
<213> ORGANISM: Artificial Sequence
<220> FEATURE:
<223> OTHER INFORMATION: anti-sense primer to construct dsRNA SoiPBAN-R

<400> SEQUENCE: 6
atccgcgggt cttaattcga gaggcgacgt tct                                33

<210> SEQ ID NO 7
<211> LENGTH: 24
<212> TYPE: DNA
<213> ORGANISM: Artificial Sequence
<220> FEATURE:
<223> OTHER INFORMATION: sense primer to construct dsRNA HezPBAN-R

<400> SEQUENCE: 7
ttaagtaaaa tggcattgtc agcg                                          24

<210> SEQ ID NO 8
<211> LENGTH: 26
<212> TYPE: DNA
<213> ORGANISM: Artificial Sequence
<220> FEATURE:
<223> OTHER INFORMATION: anti-sense primer to construct dsRNA HezPBAN-R

<400> SEQUENCE: 8
cagacgaacg aacaaaagga ctgcga                                        26

<210> SEQ ID NO 9
<211> LENGTH: 40
<212> TYPE: DNA
<213> ORGANISM: Artificial Sequence
<220> FEATURE:
<223> OTHER INFORMATION: sense primer used to construct DNA template of
      SoiPBAN-R dsRNA

<400> SEQUENCE: 9
taatacgact cactataggg accgtcgaca accgacttac                         40
```

```
<210> SEQ ID NO 10
<211> LENGTH: 40
<212> TYPE: DNA
<213> ORGANISM: Artificial Sequence
<220> FEATURE:
<223> OTHER INFORMATION: anti-sense primer used to construct DNA
      template of SoiPBAN-R dsRNA

<400> SEQUENCE: 10
taatacgact cactataggg gactctcaag aggtggtggc                           40

<210> SEQ ID NO 11
<211> LENGTH: 40
<212> TYPE: DNA
<213> ORGANISM: Artificial Sequence
<220> FEATURE:
<223> OTHER INFORMATION: sense primer used to construct DNA template of
      HezPBAN-R dsRNA

<400> SEQUENCE: 11
taatacgact cactataggg gtgtttgcat tgtgtaccgc                           40

<210> SEQ ID NO 12
<211> LENGTH: 40
<212> TYPE: DNA
<213> ORGANISM: Artificial Sequence
<220> FEATURE:
<223> OTHER INFORMATION: anti-sense primer used to construct DNA
      template of HezPBAN-R dsRNA

<400> SEQUENCE: 12
taatacgact cactataggg tataggaagg ggttgatggc                           40

<210> SEQ ID NO 13
<211> LENGTH: 29
<212> TYPE: DNA
<213> ORGANISM: Artificial Sequence
<220> FEATURE:
<223> OTHER INFORMATION: degenerate primer set
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 13
atgcaycang cncanaayta ytayytntt                                      29

<210> SEQ ID NO 14
<211> LENGTH: 10
<212> TYPE: PRT
<213> ORGANISM: Artificial Sequence
<220> FEATURE:
<223> OTHER INFORMATION: Peptide amplified by SEQ. ID. NO. 13

<400> SEQUENCE: 14

Met His Thr Ala Thr Asn Tyr Tyr Leu Phe
1               5                   10
```

<210> SEQ ID NO 15
<211> LENGTH: 29
<212> TYPE: PRT
<213> ORGANISM: Artificial Sequence
<220> FEATURE:
<223> OTHER INFORMATION: degenerate primer set

<400> SEQUENCE: 15

Gly Cys Arg Thr Gly Arg Ala Ala Asn Gly Gly Asn Gly Cys Cys Cys
1               5                   10                  15

Ala Arg Cys Ala Asp Ala Thr Arg Ala Ala Arg Ala Ala
            20                  25

<210> SEQ ID NO 16
<211> LENGTH: 10
<212> TYPE: PRT
<213> ORGANISM: Artificial Sequence
<220> FEATURE:
<223> OTHER INFORMATION: Peptide amplified by SEQ. ID. NO. 15

<400> SEQUENCE: 16

Phe Phe Ile Cys Trp Ala Pro Phe His Ala
1               5                   10

<210> SEQ ID NO 17
<211> LENGTH: 30
<212> TYPE: DNA
<213> ORGANISM: Artificial Sequence
<220> FEATURE:
<223> OTHER INFORMATION: primer used to amplify 5' cDNA ends

<400> SEQUENCE: 17
tgtgatgcct cttactgctg acggtggtca                              30

<210> SEQ ID NO 18
<211> LENGTH: 29
<212> TYPE: DNA
<213> ORGANISM: Artificial Sequence
<220> FEATURE:
<223> OTHER INFORMATION: primer used to amplify 5' cDNA ends

<400> SEQUENCE: 18
tagtaattgg tggcggtgtg catggactt                               29

<210> SEQ ID NO 19
<211> LENGTH: 26
<212> TYPE: DNA
<213> ORGANISM: Artificial Sequence
<220> FEATURE:
<223> OTHER INFORMATION: primer used to amplify 3' cDNA ends
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 19
ttyttyatht gytgggcncc nttyca                                  26

<210> SEQ ID NO 20
<211> LENGTH: 29
<212> TYPE: DNA
<213> ORGANISM: Artificial Sequence

```
<220> FEATURE:
<223> OTHER INFORMATION: primer used to amplify 3' cDNA ends

<400> SEQUENCE: 20
caccacggtg aatccgcttc tctacaata                                             29

<210> SEQ ID NO 21
<211> LENGTH: 29
<212> TYPE: DNA
<213> ORGANISM: Artificial Sequence
<220> FEATURE:
<223> OTHER INFORMATION: primer used to amplify 3' cDNA ends

<400> SEQUENCE: 21
tcaagtcgat gttgcctaaa tattgtatc                                             29

<210> SEQ ID NO 22
<211> LENGTH: 40
<212> TYPE: DNA
<213> ORGANISM: Artificial Sequence
<220> FEATURE:
<223> OTHER INFORMATION: primer used to amplify a GFP

<400> SEQUENCE: 22
taatacgact cactataggg acgtaaacgg ccacaagttc                                 40

<210> SEQ ID NO 23
<211> LENGTH: 40
<212> TYPE: DNA
<213> ORGANISM: Artificial Sequence
<220> FEATURE:
<223> OTHER INFORMATION: primer used to amplify a GFP

<400> SEQUENCE: 23
taatacgact cactataggg tgctcaggta gtggttgtcg                                 40
```

The invention claimed is:

1. An isolated double-stranded ribonucleic acid (dsRNA) for inhibiting the expression of a pheromone-biosynthesis-activating neuropeptide receptor in a cell consisting essentially of sense strand SEQ. ID. NO. 2 with the sense strand being complementary to an antisense strand.

2. The double-stranded ribonucleic acid of claim 1 wherein the double-stranded ribonucleic acid is expressed in a plant cell.

3. An isolated double-stranded ribonucleic acid (dsRNA) for inhibiting the expression of a pheromone-biosynthesis-activating neuropeptide receptor in a cell consisting essentially of sense strand SEQ. ID. NO. 4 with the sense strand being complementary to an antisense strand, wherein the double-stranded ribonucleic acid is expressed in a plant cell.

* * * * *